United States Patent [19]

Scannon et al.

[11] Patent Number: 4,590,071

[45] Date of Patent: May 20, 1986

[54] HUMAN MELANOMA SPECIFIC IMMUNOTOXINS

[75] Inventors: Patrick J. Scannon, Davis; Lynn E. Spitler, Tiburon; Howard M. Lee; Russell T. Kawahata, both of San Francisco; Ronald P. Mischak, Palo Alto, all of Calif.

[73] Assignee: Xoma Corporation, Berkeley, Calif.

[21] Appl. No.: 654,613

[22] Filed: Sep. 25, 1984

[51] Int. Cl.[4] .................. A61K 39/395; A61K 39/44; C07K 17/06
[52] U.S. Cl. ..................................... 424/85; 530/391; 530/413; 530/387
[58] Field of Search ...................... 260/112 R, 112 B; 424/85

[56] References Cited

U.S. PATENT DOCUMENTS

| | | | |
|---|---|---|---|
| 4,172,124 | 10/1979 | Koprowski et al. | 424/85 |
| 4,340,535 | 7/1982 | Voisin et al. | 260/112 |
| 4,414,148 | 11/1983 | Jansen et al. | 260/112 B |
| 4,427,653 | 1/1984 | Springer | 435/68 X |
| 4,450,154 | 5/1984 | Masuho et al. | 260/112 |
| 4,474,893 | 10/1984 | Reading | 260/112 R X |
| 4,562,160 | 12/1985 | Real et al. | 260/112 R X |

FOREIGN PATENT DOCUMENTS

| | | | |
|---|---|---|---|
| 2466252 | 4/1981 | France | 424/85 |
| 83/04312 | 12/1983 | PCT Int'l Appl. | 33/54 |
| 2142032 | 1/1985 | United Kingdom | 424/85 |

OTHER PUBLICATIONS

"Selective Killing of Normal or Neoplastic B Cells by Antibodies Coupled to the A Chain of Ricin", K. A. Krolick, et al., *Proc. Natl. Acad. Sci. USA*, vol. 77, No. 9, pp. 5419–5423, Sep. 1980.

"Monoclonal Antibody-Toxin Conjugates: Aiming the Magic Bullet", Philip E. Thorpe, et al., *Monoclonal Antibodies in Clinical Medicine*, Academic Press, pp. 168–190 (1982).

"Cytotoxicity Acquired by Conjugation of an Anti--Thy$_{1.1}$ Monoclonal Antibody and the Ribosome-Inactivating Protein, Gelonin", Philip E. Thorpe, et al., *Eur. J. Biochem.*, 116, 447–454 (1981).

"Antibody-Directed Cytotoxic Agents: Use of Monoclonal Antibody to Direct the Action of Toxin A Chains to Colorectal Carcinoma Cells", D. Gary Gilliland, et al., *Proc. Natl. Acad. Sci. USA*, vol. 77, No. 8, pp. 4539–4543, Aug. 1980.

"Fusion Between Immunoglobulin-Secreting and Nonsecreting Myeloma Cell Lines", G. Kohler, et al., *Eur. J. Immunol.*, 6:292.

"Analysis of T Lymphocyte Antibody Specificities: Comparison of Serology with Immunopercipitation Patterns", K. Horibe, et al., *Human Leucocyte Markers Detected by Monoclonal Antibodies*, Springer-Verlag, Berlin (in press).

Baenziger et al., *J. Biol. Chem.* (1979) 254:9795–9799.

Cushley et al., *Toxicon* (1984) 22(2):265.

Davidson et al., *Clinical Allergy* (1983) 13:553–561.

Panzani et al., *International Archives of Allergy* (1963) 22:350.

Simmons et al., *Analytical Biochemistry* (1985) 146:206.

Woodbury et al., *Proc. Natl. Acad. Sci.* (1980) 77:2183–2187.

Figley et al., *J. Amer. Med. Assoc.* (1928) 90:79.

Figley et al., *Journal of Allergy* (1950) 20:545.

Kornfield et al., *Biol. Chem.* (1971) 246:3259.

*Primary Examiner*—Howard E. Schain
*Attorney, Agent, or Firm*—Townsend and Townsend

[57] ABSTRACT

Conjugates of monoclonal antibodies specific to human melanoma and the A chain of a toxic lectin such as ricin or an equivalent ribosomal inhibiting protein. The conjugate is synthesized by a novel process employing anti-toxic lectin B chain antibodies to remove lectin B chain impurities and provide a highly purified conjugate that is non-toxic to cells other than melanoma. The conjugates are used to treat human melanoma.

The hybridomas XMMME-001 and XMMME-002 were deposited with the American Type Culture Collection (A.T.C.C.) on Mar. 26, 1985, and given A.T.C.C. Accession Nos. HB8759 and HB8760, respectively.

20 Claims, 8 Drawing Figures

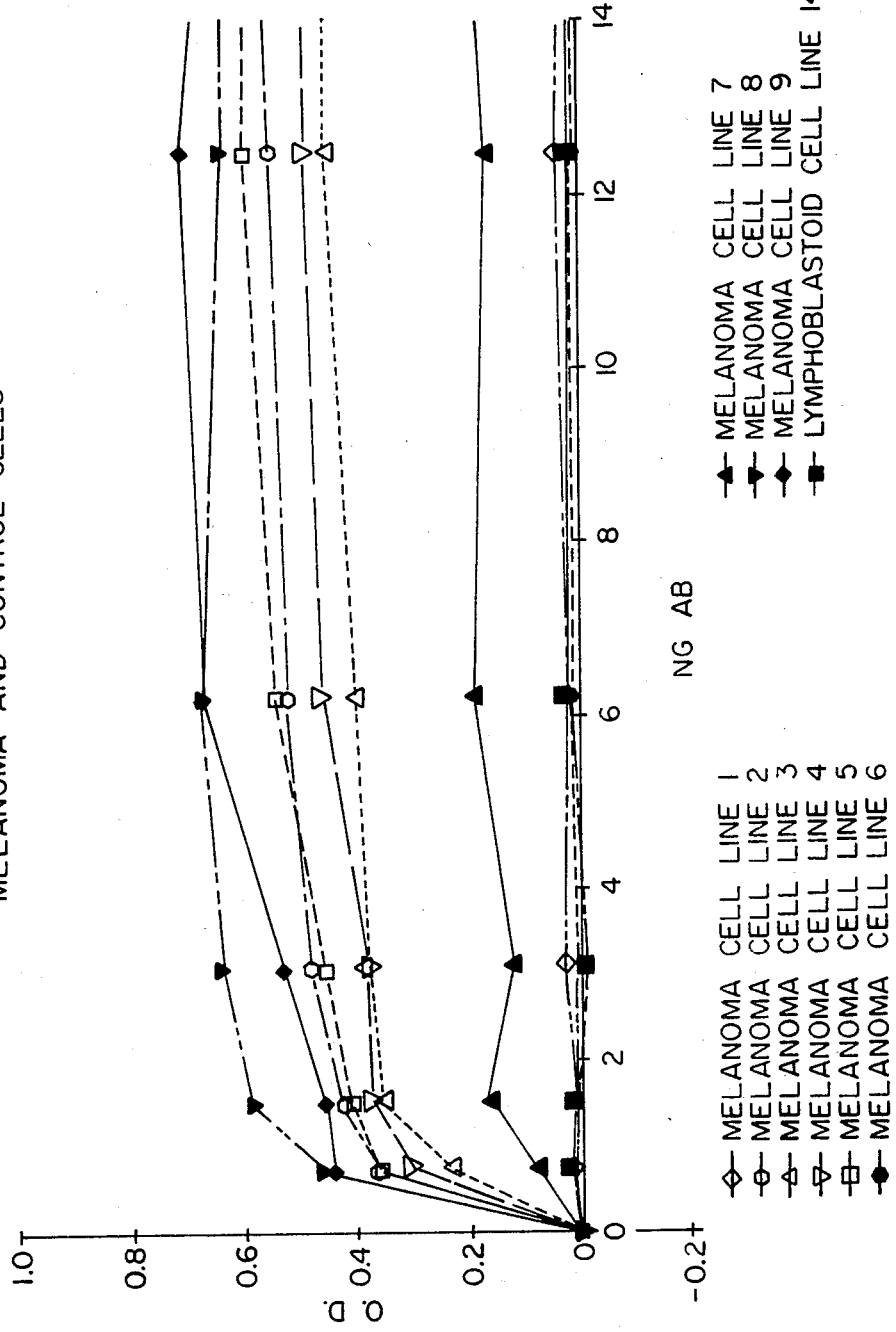
FIG.—1.

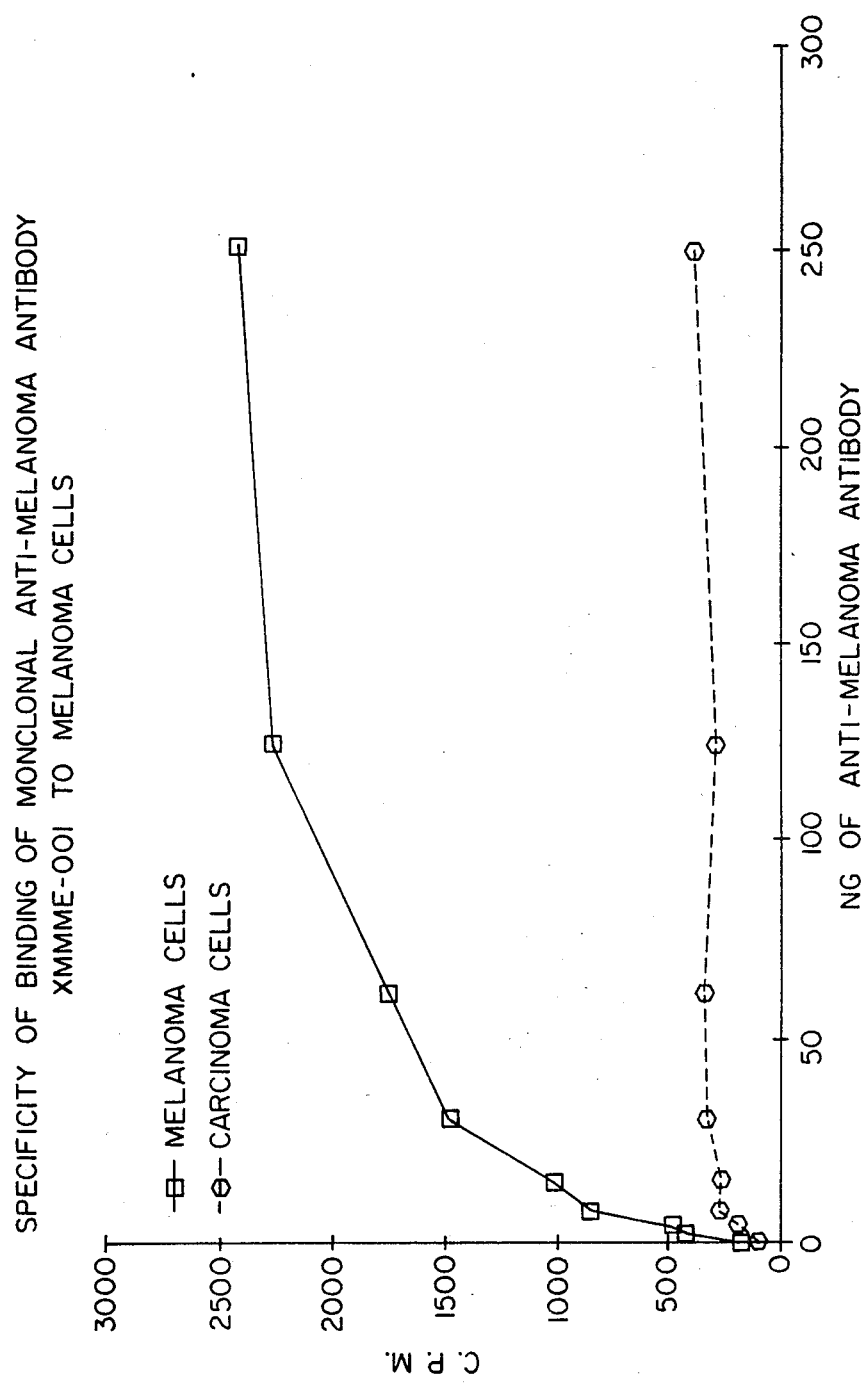

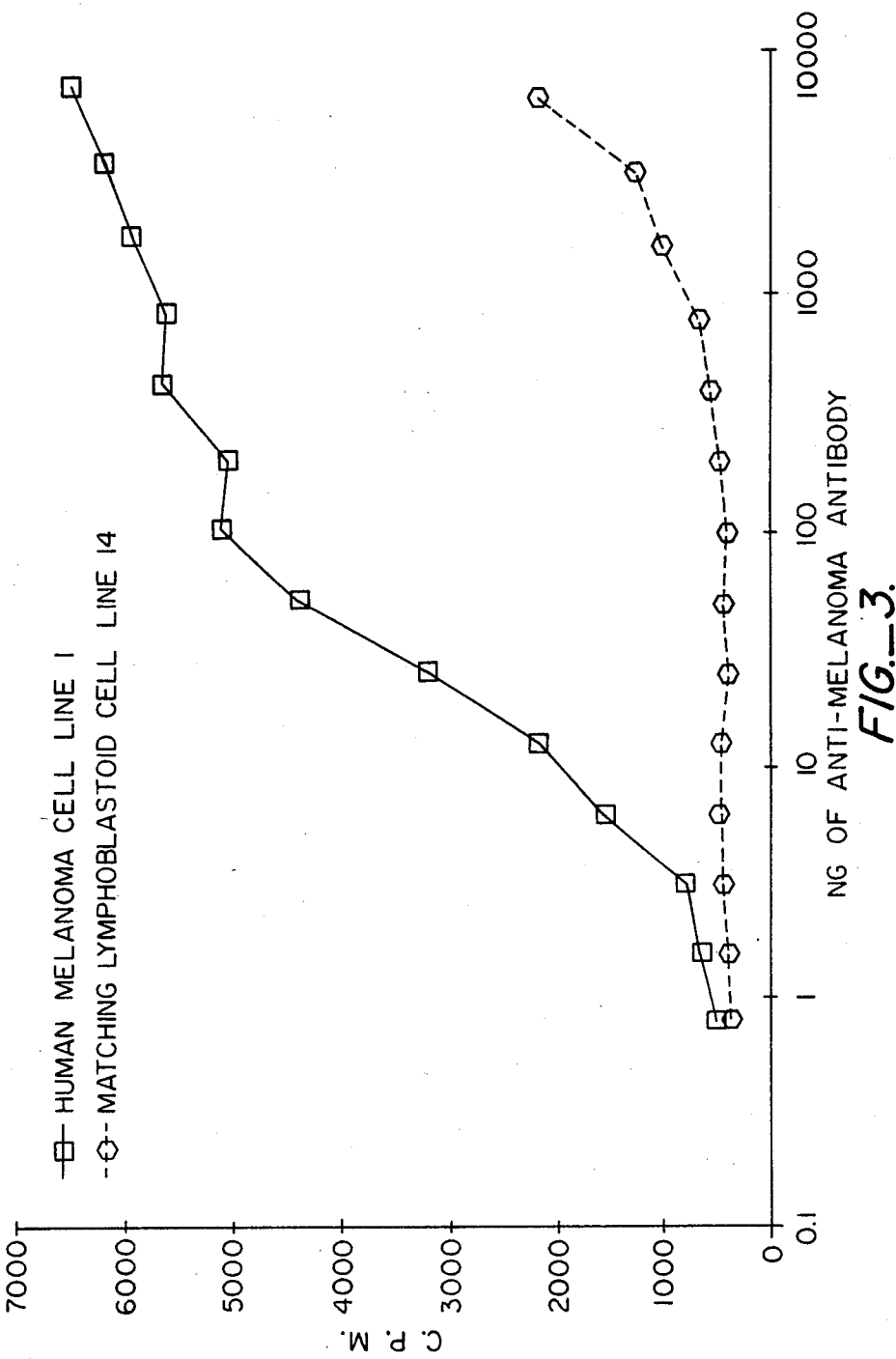

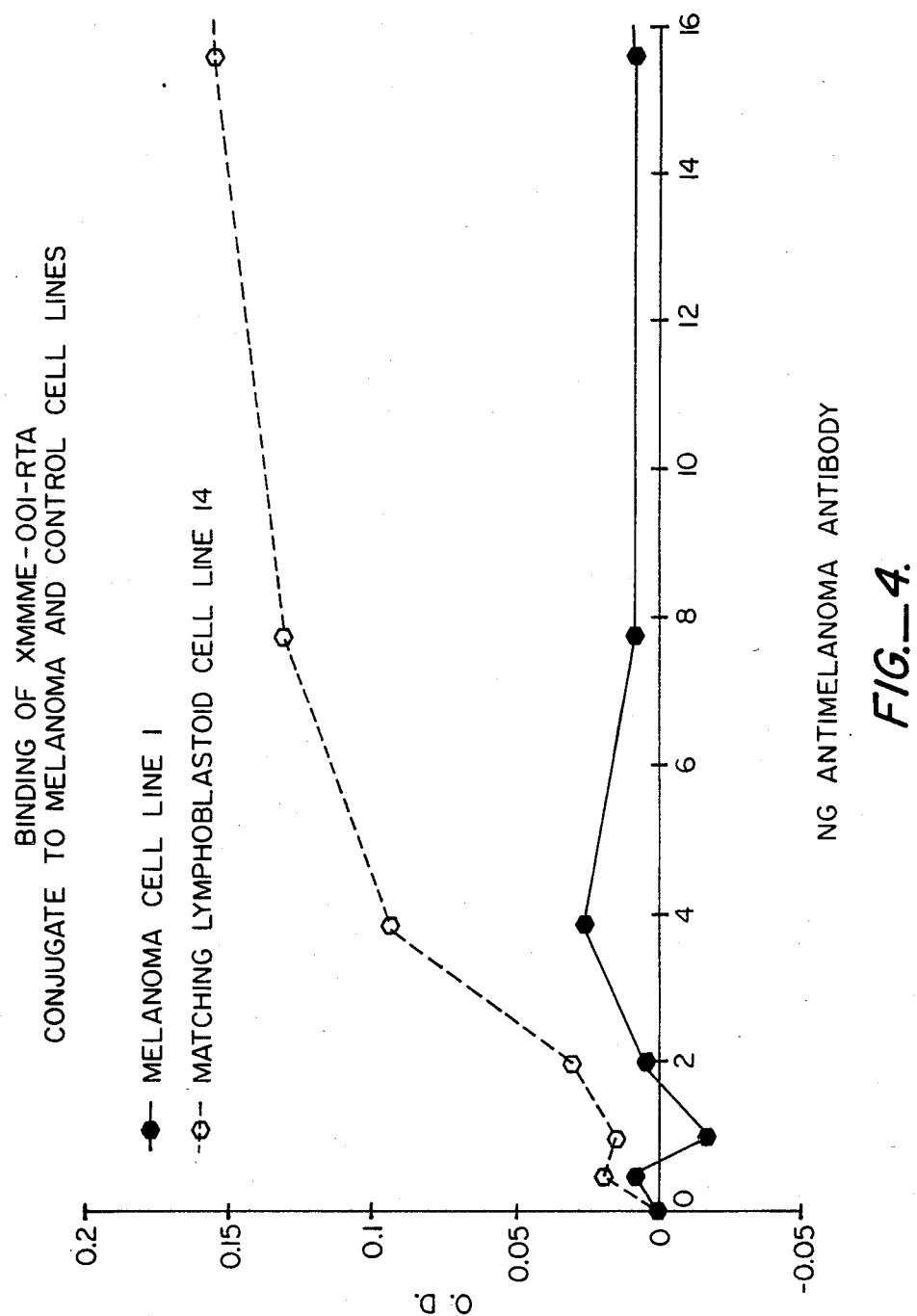

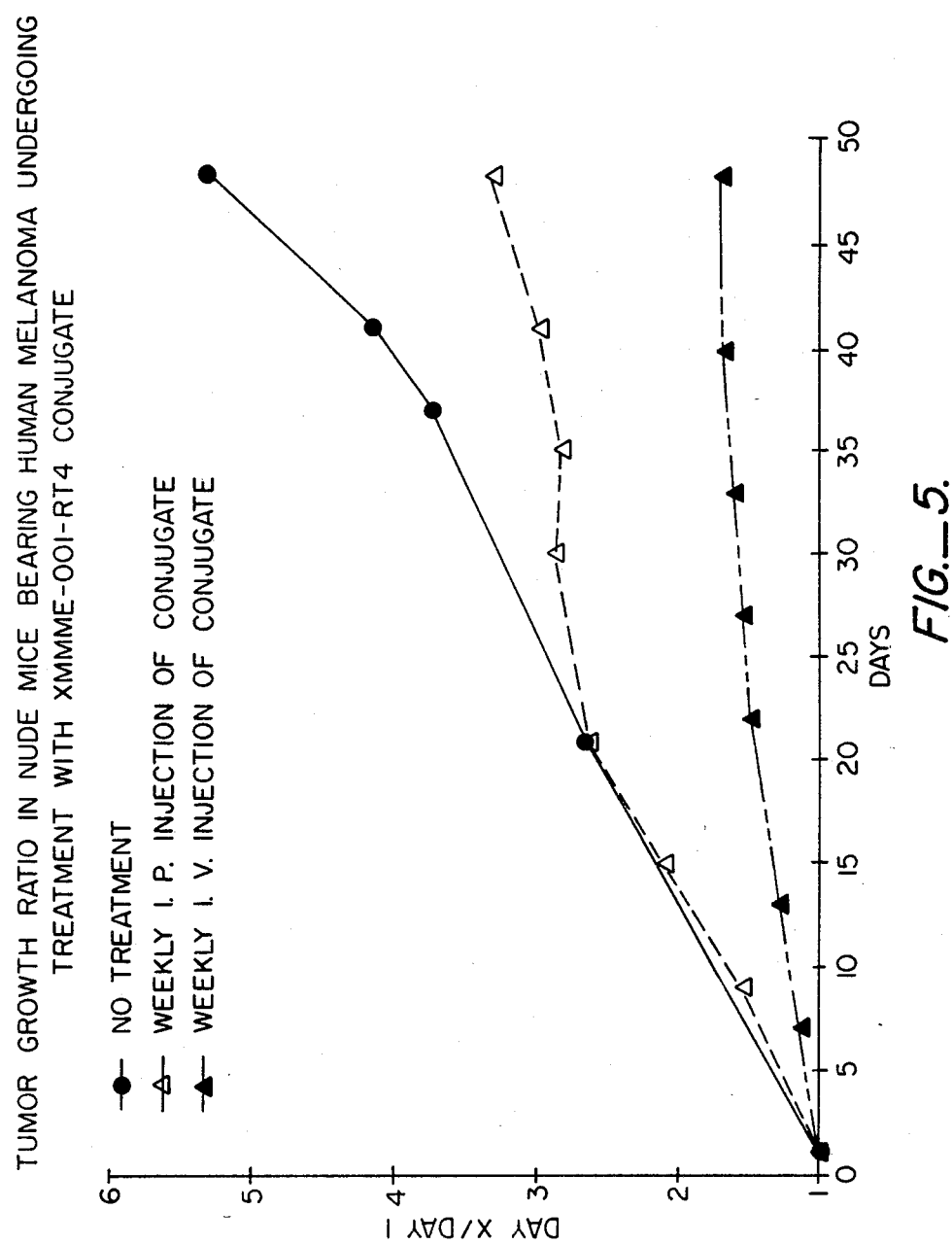
FIG._5.

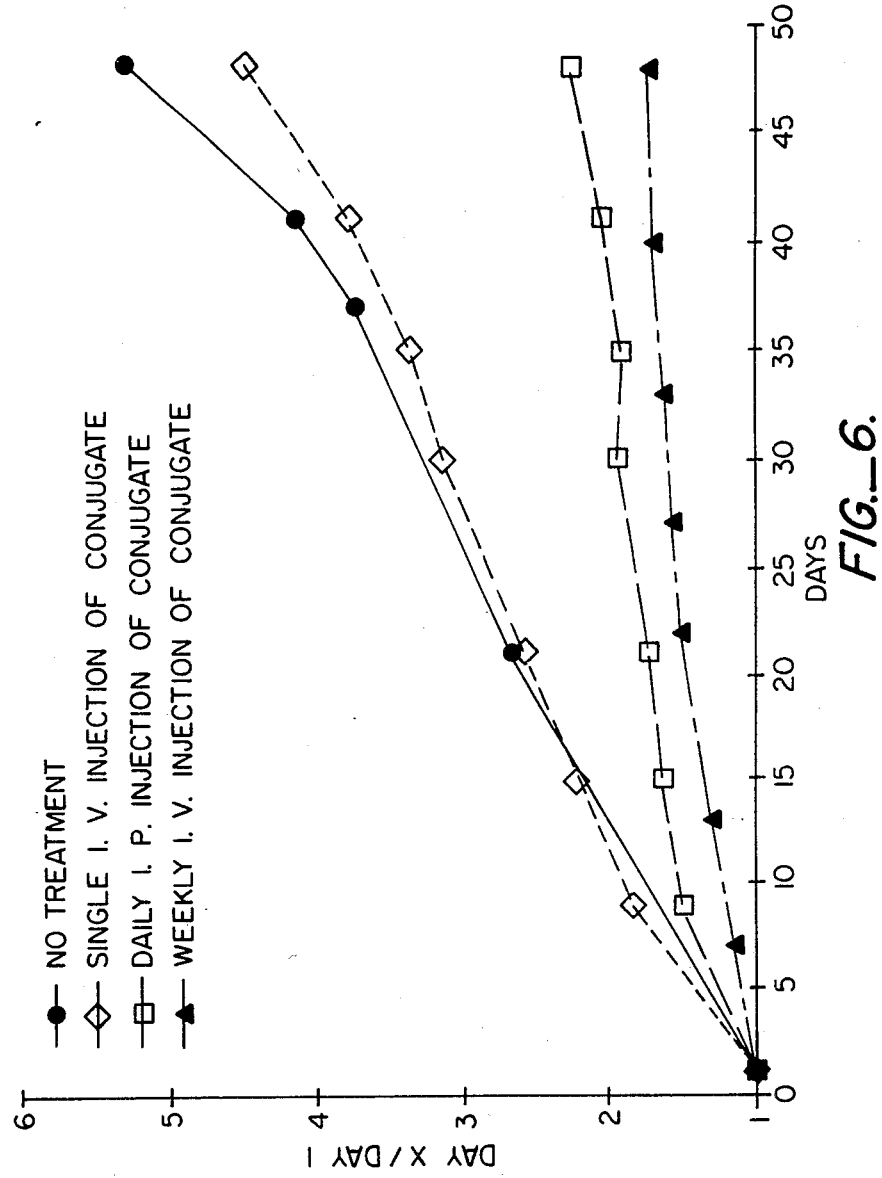

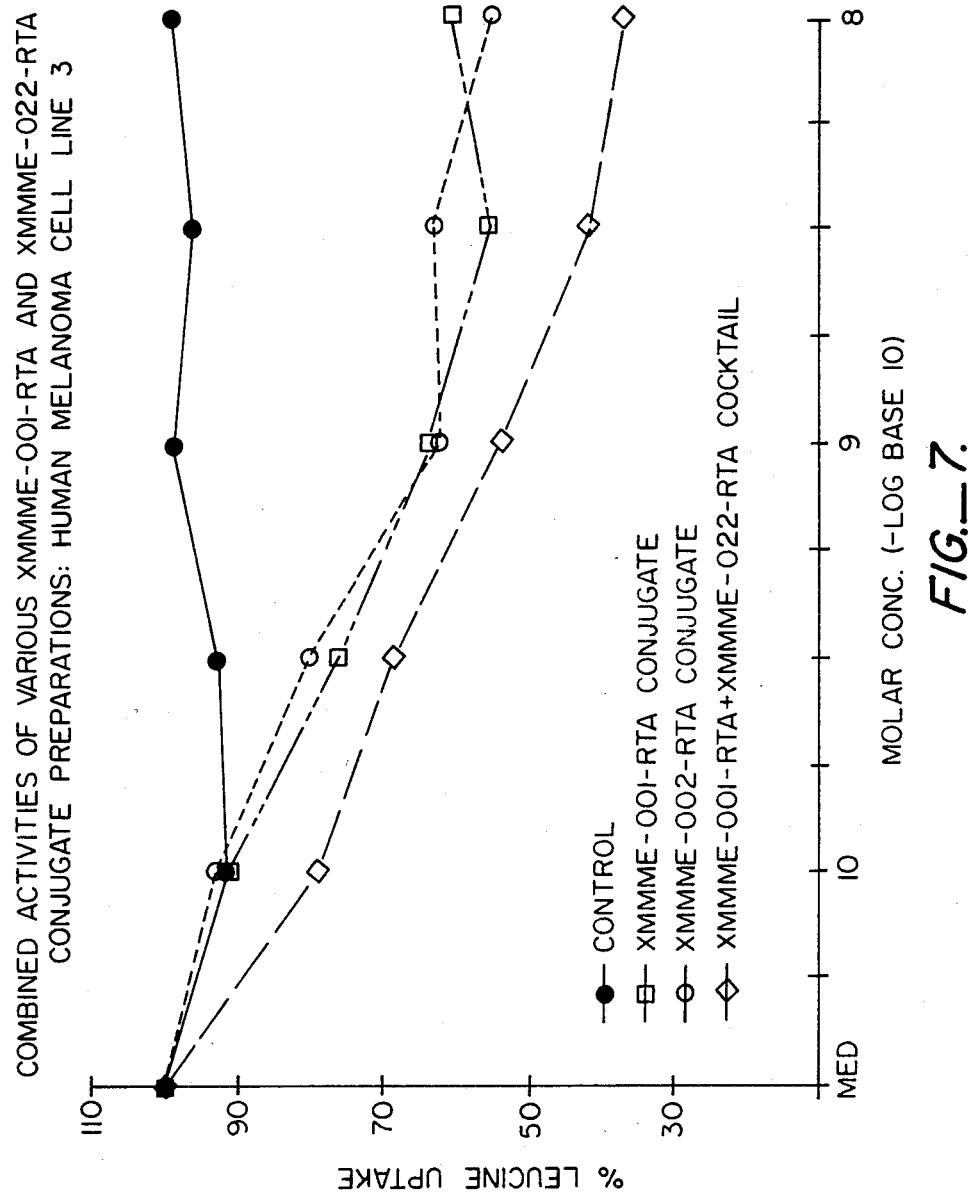
FIG._7.

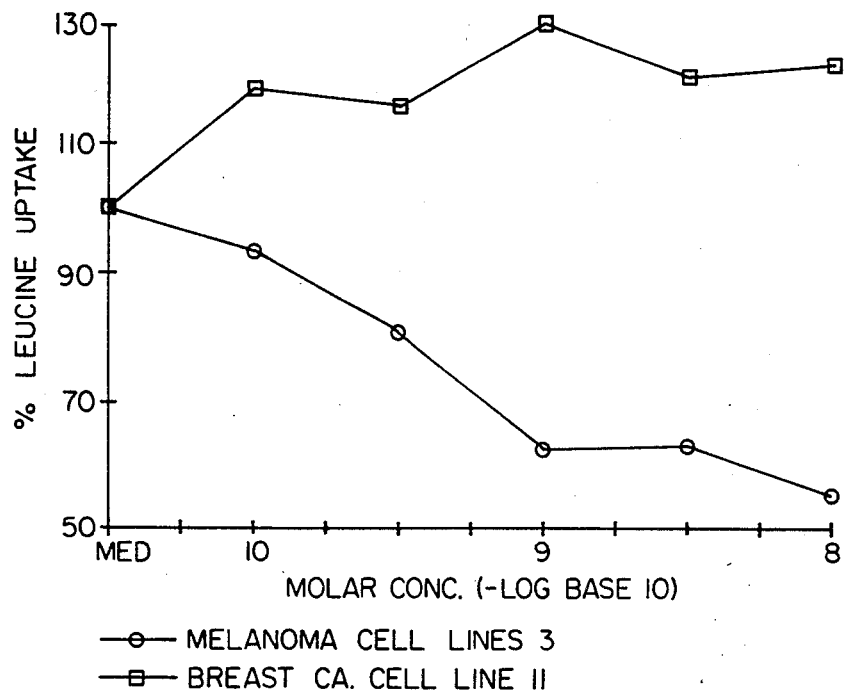
FIG._8.

HUMAN MELANOMA SPECIFIC IMMUNOTOXINS

This invention relates to cytotoxic products for the treatment of cancer and, specifically, to cytotoxic products formed by binding the A chain of a toxic lectin or its equivalent, such as the class of materials known as ribosomal inhibiting proteins (RIP), to a human melanoma specific monoclonal antibody; methods for production of such products; and, methods for the use of such products in the treatment of human melanoma.

BACKGROUND OF THE INVENTION

The use of cytotoxic products in the treatment of cancer is well known. Equally well known are the difficulties associated with such treatment. Of these difficulties, the lack of cancer-specific cytotoxicity has received considerable attention, albeit with marginal success. Cytotoxic products continue to kill cancer cells and normal cells alike. Such non-specificity results in a number of undesirable side effects for patients undergoing cancer chemotherapy with cytotoxic products including nausea, vomiting, diarrhea, hemorrhagic gastroenteritis, and hepatic and renal damage. Due to normal cell toxicity, the therapeutic dosage of cytotoxic products has been limited such that cancerous cells are not killed to a sufficient level that subsequently prevents or delays new cancerous growth.

The cytotoxic action of toxic lectins, and especially that of ricin and abrin, has been well studied. It is known that toxic lectins consist of two polypeptide chains, A and B, linked by means of disulfide bridge(s). Cytotoxicity is associated with the A chain and its inhibition of protein synthesis in nucleated cells. The B chain is essentially a delivery vehicle for the A chain. The B chain recognizes polysaccharide units at the surface of cells and creates a high affinity interaction with such units. Once the B chain binds with polysaccharide units at the cell surface, the A chain is incorporated into the cell, block ribosomal protein synthesis and untimately leading to cell death.

Toxic lectins of the type of structure and function similar to ricin include abrin, modeccin and mistletoe toxin. One other category of ribosomal inhibiting protein (RIP) is the toxin with only one subunit having functional characteristics analogous to ricin A chain. This type of RIP lacks cytotoxicity to the intact cell because of the inherent absence of a binding fragment analogous to ricin B chain. Examples of RIP's of this latter type include gelonin and pokeweed antiviral protein.

SUMMARY OF THE INVENTION

The present invention overcomes the difficulty of non-specific cytotoxicity in human melanoma chenotherapy by chemically bonding the A chain of a toxic lectin, such as ricin or abrin, with monoclonal antibodies specific to human melanoma (MoAbHM) to form cytotoxic products called conjugates using the naturally existing sulfhydryl group to form a disulfide bridge. In the conjugates, the MoAbHM assumes the role of the B chain in whole lectins. That is, the MoAbHM functions as the delivery vehicle for the toxic A chain, delivering the toxin specifically to human melanoma cells. Specificity is achieved through the selective binding activity of the monoclonal antibody with epitopes of human melanoma associated antigens. The bonding of the toxic lectin A chain to the monoclonal antibody blocks the toxic effect of the A chain until the monoclonal antibody has complexed with the human melanoma cell. The toxin is then incorporated into the cell at which point it blocks protein synthesis and the melanoma cell dies.

In a presently preferred embodiment of the invention, the conjugate comprises the XMMME-001 variety of monoclonal antibodies and the toxic A chain of the lectin ricin. Alternate embodiments of the invention include conjugates utilizing the XMMME-002 variety of monoclonal antibody, which is produced by the same method as the XMMME-001 antibody but recognizes a different epitope on the same melanoma associated antigen, and the toxic A chain of ricin.

According to the invention, any toxic lectin which may be split into A and B polypeptide chains, specifically abrin, may be used in the same way ricin is used in the preferred embodiment. In addition, any RIP, specifically gelonin and pokeweed antiviral protein, may be used in the same way as ricin A chain. Such materials are equivalent to the toxic lectin A chain for purposes of this invention.

Experiments using the invention have verified both the specificity of these cytotoxic products toward human melanoma cells and the killing of such cells.

The invention also contemplates the use of different conjugates in a therapeutic cocktail wherein a first conjugate and at least a second conjugate are administered either as a mixture, individually in a set sequence or in combination with at least one other cancer therapeutic agent.

Cytotoxic products using the A chain of a toxic lectin are known in the prior art. ["Selective Killing of Normal or Neoplastic B Cells by Antibodies Coupled to the A Chain of Ricin", K. A. Krolick, et al., *Proc. Natl. Acad. Sci. USA*, Vol. 77, No. 9, pp. 5419–5423, September 1980; "Monoclonal Antibody-Toxin Conjugates: Aiming the Magic Bullet", Philip E. Thorpe, et al., *Monoclonal Antibodies in Clinical Medicine*, Academic Press, pp. 168–190 (1982); "Cytotoxicity Acquired by Conjugation of an Anti-Thy$_{1.1}$ Monoclonal Antibody and the Ribosome-Inactivating Protein, Gelonin", Philip E. Thorpe, et al., *Eur. J. Biochem.*, 116 447–454 (1981); "Antibody-Directed Cytotoxic Agents: Use of Monoclonal Antibody to Direct the Action of Toxin A Chains to Colorectal Carcinoma Cells", D. Gary Gilliland, et al., *Proc. Natl. Acad. Sci. USA*, Vol. 77, No. 8, pp. 4539–4543, August 1980.] The present invention is an improvement over the prior art in that the purification of the A chain yields a pure product free of intact toxin molecules. This reduced toxicity permits administration of larger, more efficacious doses of the final conjugates.

According to the invention, this improved purity is achieved by running a quantity of toxic lectin A chain split from whole toxic lectin through a chromatography column containing a support media comprising antitoxic lectin B chain antibodies and modified gels. This step removes any toxic lectin B chain impurities, thus reducing recombination of the A and B chains into the more toxic whole lectin.

DETAILED DESCRIPTION OF THE PREFERRED EMBODIMENT

Materials And Methods

1. Ricin Extraction from Whole Castor Be

Ricin is extracted from the castor bean (*Ricinus communis*) by known methods. Essentially, whole castor beans are homogenized in the presence of phosphate buffered saline (PBS) with azide pH 7.2 (PBS with Azide, pH 7.0: 10mM sodium phosphate, 0.15M NaCl, 0.02% $NaN_3$, 0.5% phenylmethanesulfonyl fluoride (PMSF), pH 7.0.) The homogenate is centrifuged and the supernatant removed by vacuum aspiration leaving a bean pellet and fat lipid layer. The castor bean supernatant is precipitated with 60% ammonium sulfate (A.S.) with stirring and refrigeration. The 60% A.S. precipitate is collected by centrifugation, then dissolved in a minimum of PBS with azide, pH 7.2. This solution is then dialyzed against PBS with azide, pH 7.2 until A.S. free.

The castor bean supernatant is applied to a BioGel A-15 column. Since the ricin has a moderate affinity to the carbohydrate moieties of the column resin, this results in a delay of the elution of the toxin from the column and the separation from the run-through fraction which consists of lipids, pigments, unwanted proteins and other substances. Addition of 50 mM N-acetylgalactosamine in PBS with azide, pH 7.2 reverses the affinity of the ricin and results in a sharp peak corresponding to the elution of the bound ricin toxin.

2. Ricin Toxin A Chain Separation

The ricin toxin A chain (RTA) is separated from whole ricin obtained above by Affinity Chromatograph (AC) using an acid treated Sepharose column. (Sepharose is the exclusive trademark of Pharmacia Fine Chemicals.) Sepharose is a bead-formed gel prepared from agarose. In its natural state agarose occurs as part of the complex mixture of charged and neutral polysaccharides referred to as agar. The agarose used to make Sepharose is obtained by a purification process which removes the charged polysaccharides to give a gel with only a very small number of residual charged groups.

The column is first equilibrated with PBS with azide, pH 6.5. The ricin sample is then applied to the column and washed with PBS with azide and the eluate of non-binding proteins discarded. The column is then washed with a reducing buffer: (0.5M TRIS-HCl, pH 7.7, 1M β-mercaptoethanol, 1.2 mM EDTA.) The fraction containing the RTA is collected and dialyzed against PBS with azide, pH 6.5 until the reducing buffer has been removed. The dialyzed RTA is then filtered through glass fiber filter paper and subjected to AC again using an acid treated Sepharose column. The flow-through non-binding protein peak contains RTA and is collected. The column is then washed with PBS with azide, pH 6.5 until the entire RTA peak has been collected.

3. Ricin Toxin A Chain Purification

The RTA obtained above is purified to remove ricin toxin B chain (RTB) impurities. This step is essential to prevent increased toxicity to non-melanoma cells due to residual whole ricin toxin following separation.

The RTB is removed by first filtering the RTA fraction collected above through a glass fiber filter paper and then applying RTA to a Sepharose column previously coupled with goat anti-RTB antibodies. The flow through protein peak of RTA is collected by washing with PBS with azide, pH 6.5. After the sample is dialyzed and concentrated, the RTA is added to an equal volume of cold 100% glycerol and adjusted to $10^{-5}M$ mercaptoethanolamine and stored at $-20°$ C.

Quality control tests are performed on the purified RTA. Discontinuous SDS-PAGE on 12.5% gel indicates an absence of any contaminating band corresponding to native ricin and elicits only line bands at 33 kilodaltons (kD) and 30 kD associated with RTA isomers. IEF on LKB Ampholine PAG-plates or on Serva Servalyt Precotes failed to reveal any bands corresponding to either native recin or ricin B chain and only Coomassie Blue stained bands have appeared corresponding to RTA.

4. Human Melanoma Specific Monoclonal Antibody Production

In a presently preferred embodiment of the invention, the MoAbHM used is of the IgG2a subclass produced according to known hybridization procedures described by Kohler and Milstein, *Eur. J. Immunol.*, 6:292 (1976) with minor modifications by Hocibe, et al., described in Human Leucocyte Markers by Monoclonal Antibodies, Springer-Verlag, Berlin (in press). Cultured M21 human melanoma cells were used as the immunogen for all MoAbHM varieties including the XMMME-001 antibody produced by XMMME-001 hybridomas used in the preferred embodiment. In an alternate embodiment of the invention, the related XMMME-002 antibody is produced by the same methods. These antibodies differ in that they react with different epitopes of the same melanoma associated antigen of approximately 240 kD/>480 kD M.W.

The hybridomas XMMME-001 and XMMME-002 were deposited with the American Type Culture Collection (A.T.C.C.) on Mar. 26, 1985, and given A.T.C.C. Accession Nos. HB8759 and HB8760, respectively.

5. Reduction of RTA

RTA is reduced with dithiothreital (DTT) prior to its reaction with XMMME-001 antibody to form XMMME-001-RTA conjugates. This reduces the SH group on the RTA molecule, facilitating the formation of disulfide bridges with XMMME-001 antibody and the subsequent formation of the conjugates.

1M DTT, pH 7.0, is added to room temperature RTA solution to a final concentration of 50 mM DTT and incubated at 4° for 8–12 hours. This solution is applied to a Gel Permeation Chromatography (GPC) desalting column pre-equilibrated with phosphate buffered saline (PBS) with azide, pH 7.0 and washed with the same buffer. The first peak, which elutes in the void volume, contains RTA-SH and is collected. The RTA-SH is concentrated to a desired concentration, filtered and used in the conjugation reaction described below.

6. Thiol Group Addition to MoAbHM

Prior to the conjugation reaction, XMMME-001 antibody is activated with N-succinimidyl 3-(2-pyridyldithio)propionate (SPDP) (312 M.W.) which facilitates the formation of disulfide bridges with RTA-SH in the conjugation reaction.

An amount of XMMME-001 antibody (150,000 M.W., approximate), 10–20% more than the amount of conjugate desired, is diluted to a desired concentration with SPDP coupling buffer (0.1M NaP, 0.1M NaCl, 0.02% $NaN_3$, 0.5% PMSF), pH 7.5. If the final pH is not in the range pH 7.4–7.6, the solution is dialyzed for 8–12 hours at 0°–6° C. against a 5–50 fold or greater volume of SPDP coupling buffer. A 15X molar excess of SPDP (in absolute ethanol) is added dropwise to the XMMME-001 coupling buffer solution with vigorous stirring at room temperature.

The solution is stirred at room temperature such that the SPDP solution is immediately dispersed but not so vigorous that bubbles or frothing are generated. This solution, containing PDP-XMMME-001, is dialyzed at 0°–6° C. for 16–36 hours against PBS with azide, pH 7.0. Any visible precipitation present in the solution is removed by filtration.

7. Conjugation of XMMME-001 With RTA

The conjugation of PDP-XMMME-001 with RTA-SH is achieved by adding a 3-20X molar excess of RTA to PDP-XMMME-001 with gentle stirring. The mixture is incubated at 2°–6° C., without stirring, for 16–72 hours. The mixture is filtered if a precipitate is seen.

The conjugate of XMMME-001-RTA is purified by GPC. The mixture, containing the conjugate, XMMME-001 antibody and RTA is applied to a column pre-equilibrated with PBS with azide, pH 7.0. The column is run with upward flow and washed with PBS with azide, pH 7.0 until two peaks are eluted. The first peak, which elutes in the void volume, contains the conjugate and XMMME-001 antibody. The second peak contains RTA. The conjugate/antibody mixture is concentrated and dialyzed against PBS without azide, pH 7.0, at 1°–6° C. to remove the azide. The concentration of conjugate is calculated with the aid of a spectrophotometer. SDS-PAGE is performed on a sample of the final product as a quality control measure. The final product is sterilized by ultrafiltration and stored until needed for experimental or clinical use.

According to the invention, the dose of conjugate administered to human patients ranges from 0.01 to 20.0 milligrams of conjugate per kilogram of melanoma cell host body weight (mg/Kg) given at any one time, depending on the therapy protocol. Dilution of the respective conjugates to the desired dosage is achieved with normal saline, other isotonic solution or other injectable adjuvants.

8. Conjugate-Combination Cocktails

The use of chemotherapeutic cocktails for the treatment of cancer is well known. Different chemotherapeutic agents are often used in combination with each other and/or radiation therapy. Administration of these cocktails may be in the form of, for example, a mixture of different agents, a sequence of different agents or a combination of agents administered concurrently with radiation therapy.

According to the invention, human melanoma specific immunotoxins may be administered as therapeutic cocktails as well as separately. In one embodiment of the invention, XMMME-001-RTA conjugate is mixed with an approximately equal amount of XMMME-002-RTA conjugate, produced by the same methods as the XMMME-001-RTA conjugate, to form a cocktail for human melanoma treatment. The dose of any one conjugate, as described above, is reduced by the percentage it represents in the cocktail. For example, if XMMME-001-RTA makes up 50% of the cocktail, the dose of XMMME-001-RTA will range from 0.005 mg/Kg to 10.0 mg/Kg. This cocktail, or any other, may be delivered to the patient by a variety of clinical techniques but generally delivery will be by intravenous infusion over a period of time.

Experimental Results

A variety of in vitro and in vivo experiments utilizing the present invention in one or more embodiments confirm both specificity and cytotoxicity with respect to human melonoma cancer cells. Experimental results indicate a high binding activity on the part of the invention for a variety of human melanoma cell lines. Further, results demonstrate marked blocking of protein synthesis in melanoma cells versus normal cells.

1. In Vitro Results

As discussed above, binding specificity is achieved by replacing the lectin toxin A chain with a human melanoma specific monoclonal antibody. The antibody functions as a delivery vehicle for lectin toxin A chain. As such, the specificity of a conjugate is dependent upon the specificity of its constituent monoclonal antibody toward human melanoma cells.

A number of in vitro studies were conducted for the purpose of ascertaining the binding specificity of the XMMME-001 antibody toward a number of different human melanoma cell lines. Table 1 details the cell lines used in the various studies discussed below. The table lists the cell line code number (also referred to in the figures), the name used by the supplier, the supplier code number, the cell type and the cell lines reaction with the XMMME-001 antibody where a + indicates specificity of the antibody for the particular cell line and a − indicates no appreciable binding activity. Note that Table 1 indicates XMMME-001 specificity toward 8 of 10 human melanomas and non-specificity toward a variety of normal cells as well as several non-melanoma cancers. The binding specificity of the antibody was determined by enzyme-linked immunosorbent assay (EIA) and radioimmunoassay (RIA).

TABLE 1

SOURCES OF CELL LINES USED FOR CHARACTERIZATION OF ANTIMELANOMA ANTIBODY XMMME-001

| Code No. | Name used by Supplier | Source | Cell Type of Line | Reaction with XMMME-001 |
|---|---|---|---|---|
| 1. | Langenais B | 1 | Melanoma | + |
| 2. | Carlough B | 1 | Melanoma | + |
| 3. | Minor | 1 | Melanoma | + |
| 4. | SH#3 | 1 | Melanoma | + |
| 5. | Gilliam B | 1 | Melanoma | − |
| 6. | HS 294T | 2 | Melanoma | + |
| 7. | HS 852T | 2 | Melanoma | − |
| 8. | HS 936T C | 2 | Melanoma | + |
| 9. | HS 695 T | 2 | Melanoma | + |
| 10. | A 375 | 2 | Melanoma | + |
| 11. | MCF-7 | 3 | Breast Ca. | − |
| 12. | HT 29 | 3 | Colon Ca. | − |
| 13. | TE 85 | 4 | Osteogenic Sarcoma | − |
| 14. | Langenais LCL | 1 | Lympho-blastoid | − |
| 15. | Gilliam LCL | 1 | Lympho-blastoid | − |
| 16. | PH 342 | 3 | Fibroblast | − |
| 17. | PH 343 | 3 | Fibroblast | − |
| 18. | PH 346 | 3 | Fibroblast | − |

1. Dr. B. C. Giovanella, 918 Chenevert Street, Houston, TX 77003
2. Navy Biological Research Laboratory, Naval Supply Center, Oakland, CA
3. Peralta Cancer Research Institute, 3023 Summit, Oakland, CA 94609
4. American Type Culture Collection, 12301 Parklawn Drive, Rockville, MD 20852

FIG. 1 summarizes the results obtained by EIA studies of the binding specificity of the XMMME-001 antibody toward various human melanoma cell lines and normal lymphoblastoid cells. The ordinate represents antibody dose, the abscissa optical density. FIG. 1 shows a marked specificity of the antibody toward melanoma cell lines 1, 3, 4, 6, 8, 9. The lower level of binding seen for lines 2, 5, 7 reflect the lower level or absence of the antigen on these particular cell lines. This is most likely due to loss of antigen from the cell line due to serial tissue culture passage. The control lymphoblastoid cell line which should not have any antigen present shows on binding of the melanoma antibody XMMME-001.

Studies of the binding specificity of the XMMME-001 antibody toward non-melanoma cancers were also conducted. FIG. 2 illustrates the results of these studies utilizing RIA techniques. Again the ordinate depicts antibody dose but the abscissa shows counts per minute as obtained by using radiolabelled antibody. As may be seen in the figure, XMMME-001 antibody demonstrates little specificity toward non-melanoma carcinoma cells.

RIA techniques were also used to assay studies of the specificity of the antibody with respect to melanoma and lymphoblastoid cells from the same host. The results, summarized in FIG. 3, show a high degree of specificity for the melanoma cells and little binding activity with the lymphoblastoid cells until high doses of antibody are present. Same-host studies were repeated with a conjugate of the XMMME-001 antibody and RTA. These studies, summarized in FIG. 4, indicate specificity of the XMMME-001 RTA conjugate toward the melanoma cells with little binding activity with the matching lymphoblastoid cell line.

The fact that the antibody does not react with lymphoblastoid cells from the same human host as the melanoma cells demonstrates reactivity of the antibody with melanoma associated antigens as opposed to human leukocyte antigen (HLA). Reactivity with HLA has been a problem associated with monoclonal antibodies in the prior art.

2. In Vivo Results

A number of studies using MoAbHM and conjugates of MoAbHM and RTA have been performed on athymic (nude) mice bearing human melanoma tumors. These have been tumor growth studies wherein tumors were measured and surface area calculated periodically over 35 or more days post-treatment. Table II illustrates the results obtained from a number of studies conducted to determine the efficacy of several therapy regimes using the XMMME-001-RTA conjugate. The table details the treatment regime, the administration route (interperitoneal or i.p., and intravenous or i.v.), dose of conjugate (in micrograms), the number of animals used in the particular study, the ratio on day 35 (the area of the tumor on day 35/the area of the tumor on the day treatment started) and the p Value. As can be seen from the table, the greatest efficacy was demonstrated by the administration of the conjugate i.v. on a weekly basis to a total dose of 100 μg per week at the rate of 20 μg per day for five days per week.

FIGS. 5 and 6 graphically illustrate further efficacy studies with nude mice bearing human melanoma tumors. FIG. 5 summarizes the results of studies comparing weekly i.p. versus weekly i.v. injection of XMMME-001-RTA conjugate. Note that weekly i.v. administration substantially reduced tumor growth. FIG. 6 summarizes the results of studies comparing single i.v. injection of conjugate with weekly i.p. and weekly i.v. injection. Again, the weekly i.v. injection (100 μg per week) showed the greatest efficacy with respect to suppressing tumor growth.

3. In Vitro Cocktail Results

The combined activities of the XMMME-001-RTA and XMMME-002-RTA conjugates were studied in vitro using human melanoma cell line 3 (Minor). The results are summarized in FIG. 7. Referring to FIG. 7, note that the ordinate represents molar concentration ($-\log 10$) and the abscissa percent of radiolabelled leucine uptake. The percent of leucine uptake is a measure of protein synthesis by nucleated cells. The lower the percent of leucine uptake, the less protein synthesis by the cell.

As may be seen from FIG. 7, both the XMMME-001-RTA and XMMME-002-RTA conjugates inhibit protein synthesis in melanoma cells but not in the control cells. A cocktail of approximately equal amounts of XMMME-001-RTA and XMMME-002-RTA conjugates was also studied. Note that the cocktail demonstrated significantly greater inhibition of protein synthesis than either of the conjugates individually.

The killing specificity of the XMMME-001-RTA plus XMMME-002-RTA cocktail was studied in vitro using melanoma cell line 3 and breast carcinoma cell line 11. The results of these studies are summarized in FIG. 8 as a function of percent leucine uptake as in FIG. 7. The cocktail demonstrates a high degree of specificity toward the melanoma cell line with no demonstrable activity toward the breast carcinoma cells.

We claim:

1. A cytotoxic conjugate, comprising a lectin A chain purified with anti-lectin B chain antibodies bound to a monoclonal antibody that binds substantially only human melanoma associated antigen to about 240 kD/480 kD m.w.

2. The conjugate as claimed in claim 1, wherein the monoclonal antibody is that produced by hybridoma XMMME-001 having A.T.C.C. Accession No. HB8759.

3. The conjugate as claimed in claim 1, wherein the monoclonal antibody is that produced by hybridoma XMMME-002 having A.T.C.C. Accession No. HB8760.

TABLE II

RESULTS OF THERAPY WITH ANTIMELANOMA ANTIBODY RICIN A CHAIN CONJUGATES IN NUDE MICE BEARING HUMAN MELANOMAS

| TREATMENT | ROUTE | DOSE OF CONJUGATE | NO. OF ANIMALS | RATIO ON DAY 35* |
|---|---|---|---|---|
| NONE | — | — | 20 | 3.7 ± 0.4 |
| CONJUGATE, SINGLE INJECTION | iv | 250 μg | 4 | 3.4 ± 0.3(.686)+ |
| CONJUGATE, WEEKLY INJECTIONS | ip | 100 μg | 8 | 2.8 ± 0.2(.157) |
| CONJUGATE, WEEKLY INJECTIONS | iv | 100 μg | 6 | 1.6 ± 0.2(.006) |
| CONJUGATE, DAILY INJECTION | ip | 100 μg | 6 | 1.9 ± 0.4(.018) |

*Ratio: Area of tumor on day 35/area of tumor on day treatment started.
+Numbers in parentheses represent p values, two tailed.

4. The conjugate as claimed in claim 1, wherein the lectin A chain is abrin A chain purified with anti-abrin B chain antibodies.

5. A cytotoxic therapeutic cocktail comprising a first conjugate of a lectin A chain purified with anti-lectin B chain antibodies bound to a monoclonal antibody that binds substantially only human melanoma associated antigen of about 240 kD/480 kD m.w. and a second conjugate of a lectin A chain purified with anti-lectin B chain antibodies bound to a different monoclonal antibody that binds substantially only human melanoma associated antigen of about 240 kD/480 kD m.w. than in the first conjugate.

6. The cocktail as claimed in claim 5, wherein the monoclonal antibody of the first conjugate is that produced by hybridoma XMMME-001 having A.T.C.C. Accession No. HB8759.

7. The cocktail as claimed in claim 5, wherein the monoclonal antibody of the first conjugate is that produced by hybridoma XMMME-002 having A.T.C.C. Accession No. HB8760.

8. The cocktail as claimed in claim 6, wherein the monoclonal antibody of the second conjugate is that produced by hybridoma XMMME-002 having A.T.C.C. Accession No. HB8760.

9. The cocktail as claimed in claim 5, wherein the lectin A chain of the first and second conjugates is abrin A chain purified with anti-abrin B chain antibodies.

10. The cocktail as claimed in claim 5, wherein the lectin A chain of the first conjugate is ricin A chain purified with anti-ricin B chain antibodies and the lectin A chain of the second conjugate is abrin A chain purified with anti-abrin B chain antibodies.

11. A method for the treatment of human melanoma cells, comprising administering a therapeutic dose of the conjugate claimed in claim 1 to a human melanoma cell host.

12. A method for the treatment of human melanoma cells, comprising administering a therapeutic dose of the cocktail claimed in claim 5 to a human melanoma cell host.

13. A method for the treatment of human melanoma cells, comprising administering approximately 0.01 to 20.0 milligrams of the conjugate claimed in claim 1 to a melanoma cell host per kilogram of host body weight.

14. A method for the treatment of human melanoma cells, comprising administering the clocktail claimed in claim 5 to a melanoma cell host, wherein the total dose of all conjugates is in the approximate range of 0.01 to 20.0 milligrams per kilogram of host body weight.

15. Antibodies having substantially the same specificity as antibodies produced by hybridoma XMMME-001 having A.T.C.C. Accession No. HB8759 which produces antibodies that bind substantially only human melanoma associated antigens of about 240 kD/480 kD m.w.

16. Antibodies having substantially the same specificity as antibodies produced by hybridoma XMMME-002 having A.T.C.C. Accession No. HB8760 which produces antibodies that bind substantially only human melanoma associated antigens of about 240 kD/480 kD m.w.

17. Hybridoma XMMME-001 having A.T.C.C. Accession No. HB8759 which produces antibodies that bind substantially only human melanoma associated antigens of about 240 kD/480 kD m.w.

18. Hybridoma XMMME-002 having A.T.C.C. Accession No. HB8760 which produces antibodies that bind substantially only human melanoma associated antigens of about 240 kD/480 kD m.w.

19. A cytotoxic conjugate, comprising ricin A chain purified with anti-ricin B chain antibodies bound to a monoclonal antibody that binds substantially only human melanoma associated antigen of about 240 kD/480 kD m.w.

20. A cytotoxic therapeutic cocktail comprising a first conjugate of ricin A chain, purified with anti-ricin B chain antibodies, bound to a monoclonal antibody that binds substantially only human melanoma associated antigen of about 240 kD/480 kD m.w., and a second conjugate of ricin A chain, purified with anti-ricin B chain antibodies, bound to a different monoclonal antibody than in the first conjugate, that binds substantially only human melanoma associated antigen of about 240 kD/480 kD m.w.

* * * * *